(12) United States Patent
Inch et al.

(10) Patent No.: US 11,812,747 B2
(45) Date of Patent: Nov. 14, 2023

(54) METHODS OF PROTECTING A PLANT FROM FUNGAL PESTS

(71) Applicant: NOVOZYMES BIOAG A/S, Bagsvaerd (DK)

(72) Inventors: Sharon Inch, Durham, NC (US); Tine Hoff, Holte (DK); Michael Frodyma, Roanoke, VA (US); Michelle Maranta, Davis, CA (US); Barbara Cherry, Winters, CA (US)

(73) Assignee: NOVOZYMES BIOAG A/S, Bagsvaerd (DK)

( * ) Notice: Subject to any disclaimer, the term of this patent is extended or adjusted under 35 U.S.C. 154(b) by 483 days.

(21) Appl. No.: 16/965,054

(22) PCT Filed: Feb. 6, 2019

(86) PCT No.: PCT/US2019/016860
§ 371 (c)(1),
(2) Date: Jul. 27, 2020

(87) PCT Pub. No.: WO2019/157061
PCT Pub. Date: Aug. 15, 2019

(65) Prior Publication Data
US 2021/0106013 A1    Apr. 15, 2021

Related U.S. Application Data

(60) Provisional application No. 62/626,940, filed on Feb. 6, 2018.

(51) Int. Cl.
*A01N 63/50*   (2020.01)
*A01N 25/28*   (2006.01)
*A01N 37/46*   (2006.01)

(52) U.S. Cl.
CPC ............. *A01N 37/46* (2013.01); *A01N 25/28* (2013.01); *A01N 63/50* (2020.01)

(58) Field of Classification Search
CPC ......... A01N 37/46; A01N 63/50; A01N 25/28
See application file for complete search history.

(56) References Cited

U.S. PATENT DOCUMENTS

| | | |
|---|---|---|
| 2005/0054072 A1 | 3/2005 | Norregaard-Madsen |
| 2005/0244922 A1 | 11/2005 | Andersen |
| 2007/0010417 A1 | 1/2007 | Wieland |
| 2008/0050774 A1 | 2/2008 | Berka |
| 2010/0196990 A1 | 8/2010 | Svendsen |
| 2011/0117624 A1 | 5/2011 | Norregaard-Madsen |
| 2017/0156342 A1* | 6/2017 | Gerhardt ................ A01N 63/22 |

FOREIGN PATENT DOCUMENTS

WO   2011/161135 A1   12/2011

OTHER PUBLICATIONS

Encyclopedia Britannica definition of "Missense Mutation," downloaded Feb. 17, 2023 from https://www.britannica.com/science/missense-mutation. (Year: 2023).*

* cited by examiner

*Primary Examiner* — Michael P Cohen
(74) *Attorney, Agent, or Firm* — Adam Rucker

(57) ABSTRACT

A method of controlling or preventing pathogenic damage and/or pest damage in a plant propagation material, a plant, part of a plant and/or plant organ, comprising applying on the plant, part of the plant, plant organ, plant propagation material or a surrounding area thereof a phytoprotective agent comprising a protease.

20 Claims, No Drawings
Specification includes a Sequence Listing.

METHODS OF PROTECTING A PLANT FROM FUNGAL PESTS

CROSS-REFERENCE TO RELATED APPLICATIONS

This application is a 35 U.S.C. 371 national application of international application no. PCT/US2019/016860 filed Feb. 6, 2019, which claims priority or the benefit under 35 U.S.C. 119 of U.S. provisional application No. 62/626,940 filed Feb. 6, 2018, the contents of which are fully incorporated herein by reference.

REFERENCE TO A SEQUENCE LISTING

This application contains a Sequence Listing in computer readable form, which is incorporated herein by reference.

BACKGROUND

Because of increasing populations and corresponding demands for more efficient and productive farms, there remains a need for new methods for protecting crops and plants from disease and pests thereby preventing waste and economic loss while improving crop yields and ensuring a sufficient global food supply.

SUMMARY OF THE CLAIMED INVENTION

The present disclosure provides methods for of controlling or preventing pathogenic damage and/or pest damage in a plant propagation material, a plant, part of a plant and/or plant organ, comprising applying on the plant, part of the plant, plant organ, plant propagation material or a surrounding area thereof a phytoprotective agent comprising a protease.

DETAILED DESCRIPTION

This description is not intended to be a detailed catalog of all the different ways in which the invention may be implemented or of all the features that may be added to the instant invention. For example, features illustrated with respect to one embodiment may be incorporated into other embodiments and features illustrated with respect to a particular embodiment may be deleted from that embodiment. In addition, numerous variations and additions to the various embodiments suggested herein, which do not depart from the instant invention, will be apparent to those skilled in the art in light of the instant disclosure. Hence, the following description is intended to illustrate some particular embodiments of the invention and not to exhaustively specify all permutations, combinations and variations thereof.

The terminology used herein is for the purpose of describing particular embodiments only and is not intended to be limiting of the invention.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the specification and relevant art and should not be interpreted in an idealized or overly formal sense unless expressly so defined herein. For the sake of brevity and/or clarity, well-known functions or constructions may not be described in detail.

As used herein, the singular forms "a," "an," and "the" are intended to include the plural forms as well, unless the context clearly indicates otherwise.

As used herein, the terms "acaricide" and "acaricidal" refer to an agent or combination of agents the application of which is toxic to an acarid (i.e., kills an acarid, inhibits the growth of an acarid and/or inhibits the reproduction of an acarid).

As used herein, the term "agriculturally beneficial agent" refers to any agent (e.g., chemical or biological agent) or combination of agents the application of which causes or provides a beneficial and/or useful effect in agriculture including, but not limited to, agriculturally beneficial microorganisms, biostimulants, nutrients, pesticides (e.g., acaricides, fungicides, herbicides, insecticides, and nematicides) and plant signal molecules.

As used herein, the term "agriculturally beneficial microorganism" refers to a microorganism having at least one agriculturally beneficial property (e.g., the ability to fix nitrogen, the ability to solubilize phosphate and/or the ability to produce an agriculturally beneficial agent, such as a plant signal molecule).

As used herein, the term "agriculturally acceptable carrier" refers to a substance or composition that can be used to deliver an agriculturally beneficial agent to a plant, plant part or plant growth medium (e.g., soil) without causing/having an unduly adverse effect on plant growth and/or yield. As used herein, the term "foliar-compatible carrier" refers to a material that can be foliarly applied to a plant or plant part without causing/having an unduly adverse effect on the plant, plant part, plant growth, plant health, or the like. As used herein, the term "seed-compatible carrier" refers to a material that can be applied to a seed without causing/having an unduly adverse effect on the seed, the plant that grows from the seed, seed germination, or the like. As used herein, the term "soil-compatible carrier" refers to a material that can be added to a soil without causing/having an unduly adverse effect on plant growth, soil structure, soil drainage, or the like.

As used herein, the term "and/or" is intended to include any and all combinations of one or more of the associated listed items, as well as the lack of combinations when interpreted in the alternative ("or"). Thus, the phrase "A, B and/or C" is to be interpreted as "A, A and B, A and B and C, A and C, B and C, or C."

As used herein, the terms "associated with," in association with" and "associated therewith," when used in reference to a relationship between a composition of the present disclosure and a plant or plant part, refer to at least a juxtaposition or close proximity of the composition and the plant or plant part. Such a juxtaposition or close proximity may be achieved by contacting or applying the composition directly to the plant or plant part and/or by applying the composition to the plant growth medium (e.g., soil) in which the plant or plant part will be grown (or is currently being grown). According to some embodiments, the composition is applied as a coating to the outer surface of the plant or plant part. According to some embodiments, the composition is applied to soil at, near or surrounding the site in which the plant or plant part will be grown (or is currently being grown).

As used herein, the term "aqueous" refers to a composition that contains more than a trace amount of water (i.e., more than 0.5% water by weight, based upon the total weight of the composition).

As used herein, the term "consists essentially of," when used in reference to inoculant compositions and methods of the present disclosure, means that the compositions/methods may contain additional components/steps so long as the additional components/steps do not materially alter the composition/method. The term "materially alter," as applied to a composition/method of the present disclosure, refers to an increase or decrease in the effectiveness of the composition/method of at least 20%.

As used herein, the term "dispersant" refers to an agent or combination of agents the application of which reduces the cohesiveness of like particles, the surface tension of a liquid, the interfacial tension between two liquids and/or the interfacial tension between or a liquid and a solid.

As used herein, the terms "effective amount," "effective concentration" and "effective amount/concentration" refer to an amount or concentration that is sufficient to cause a desired effect (e.g. reduced disease severity). The absolute value of the amount/concentration that is sufficient to cause the desired effect may be affected by factors such as the type and magnitude of effect desired, the type, size and volume of material to which the compositon will be applied, the type(s) of phytoprotective agent in the composition, the amount of phytoprotective agent in the composition, the stability of the phytoprotective agent in the composition and the storage conditions (e.g., temperature, relative humidity, duration). Those skilled in the art will understand how to select an effective amount/concentration using routine dose-response experiments.

As used herein, the terms "enhanced growth" and "enhanced plant growth" refer to an improvement in one or more characteristics of plant growth and/or development as compared to one or more control plants (e.g., a plant germinated from an untreated seed or an untreated plant). Exemplary plant growth/development characteristics include, but are not limited to, biomass, carbohydrate biosynthesis, chlorophyll content, cold tolerance, drought tolerance, height, leaf length, leaf mass, leaf number, leaf surface area, leaf volume, nutrient uptake (e.g., calcium, iron, magnesium, nitrogen, phosphorous, potassium and/or sulfur uptake), rate(s) of photosynthesis, root area, root diameter, root length, root mass, root nodulation (e.g., nodule mass, nodule number, nodule volume), root number, root surface area, root volume, salt tolerance, seed germination, seedling emergence, shoot diameter, shoot length, shoot mass, shoot number, shoot surface area, shoot volume, spread, stomatal conductance and survival rate. Unless otherwise indicated, references to enhanced plant growth are to be interpreted as meaning that compositions and methods of the present disclosure enhance plant corn growth by controlling or preventing pathogenic damage and/or pest damage in a plant propagation material, a plant, part of a plant and/or plant organ, enhancing nutrient availability, improving soil characteristics, etc. and are not to be interpreted as suggesting that compositions and methods of the present disclosure act as plant growth regulators.

As used herein, the terms "enhanced yield" and "enhanced plant yield" refer to an improvement in one or more characteristics of plant yield as compared to one or more control plants (e.g., a control plant germinated from an untreated seed). Exemplary plant yield characteristics include, but are not limited to, biomass; bushels per acre; grain weight per plot (GWTPP); nutritional content; percentage of plants in a given area (e.g., plot) that fail to produce grain; yield at standard moisture percentage (YSMP), such as grain yield at standard moisture percentage (GYSMP); yield per plot (YPP), such as grain weight per plot (GWTPP); and yield reduction (YRED). Unless otherwise indicated, references to enhanced plant yield are to be interpreted as meaning that compositions and methods of the present disclosure enhance plant yield by controlling or preventing pathogenic damage and/or pest damage in a plant propagation material, a plant, part of a plant and/or plant organ, enhancing nutrient availability, improving soil characteristics, etc. and are not to be interpreted as suggesting that compositions and methods of the present disclosure act as plant growth regulators.

As used herein, the term "foliage" refers to those portions of a plant that normally grow above the ground, including, but not limited to, leaves, stalks, stems, flowers, fruiting bodies and fruits.

As used herein, the terms "foliar application" and "foliarly applied" refer to the application of the composition of the present disclosure to the foliage of a plant (e.g., to the leaves of the plant). Application may be effected by any suitable means, including, but not limited to, spraying the plant with the composition of the present disclosure. In some embodiments, the composition of the present disclosure is/are applied to the leaves, stems and/or stalk of the plant and not to the flowers, fruiting bodies or fruits of the plant.

As used herein, the terms "fungicide" and "fungicidal" refer to an agent or combination of agents the application of which is toxic to a fungus (i.e., kills a fungus, inhibits the growth of a fungus and/or inhibits the reproduction of a fungus).

As used herein, the terms "herbicide" and "herbicidal" refer to an agent or combination of agents the application of which is toxic to a weed (i.e., kills a weed, inhibits the growth of a weed and/or inhibits the reproduction of a weed).

As used herein, the terms "insecticide" and "insecticidal" refer to an agent or combination of agents the application of which is toxic to an insect (i.e., kills an insect, inhibits the growth of an insect and/or inhibits the reproduction of an insect).

As used herein, the term "isomer" includes all stereoisomers of the compounds and/or molecules to which it refers, including enantiomers and diastereomers, as well as all conformers, roatmers and tautomers, unless otherwise indicated. Compounds and/or molecules disclosed herein include all enantiomers in either substantially pure levorotatory or dextrorotatory form, or in a racemic mixture, or in any ratio of enantiomers. Where embodiments disclose a (D)-enantiomer, that embodiment also includes the (L)-enantiomer; where embodiments disclose a (L)-enantiomer, that embodiment also includes the (D)-enantiomer. Where embodiments disclose a (+)-enantiomer, that embodiment also includes the (−)-enantiomer; where embodiments disclose a (−)-enantiomer, that embodiment also includes the (+)-enantiomer. Where embodiments disclose a (S)-enantiomer, that embodiment also includes the (R)-enantiomer; where embodiments disclose a (R)-enantiomer, that embodiment also includes the (S)-enantiomer. Embodiments are intended to include any diastereomers of the compounds and/or molecules referred to herein in diastereomerically pure form and in the form of mixtures in all ratios. Unless stereochemistry is explicitly indicated in a chemical structure or chemical name, the chemical structure or chemical name is intended to embrace all possible stereoisomers, conformers, rotamers and tautomers of compounds and/or molecules depicted.

As used herein, the terms "nematicide" and "nematicidal" refer to an agent or combination of agents the application of which is toxic to a nematode (i.e., kills a nematode, inhibits the growth of a nematode and/or inhibits the reproduction of a nematode).

As used herein, the term "nitrogen fixing organism" refers to an organism capable of converting atmospheric nitrogen ($N_2$) into a form that may be utilized by a plant or plant part (e.g., ammonia ($NH_3$), ammonium ($NH_4^+$), etc.).

As used herein, the term "non-aqueous" refers to a composition that comprises no more than a trace amount of water (i.e., no more than 0.5% water by weight, based upon the total weight of the composition).

As used herein, the term "nutrient" refers to a compound or element useful for nourishing a plant (e.g., vitamins, macrominerals, micronutrients, trace minerals, organic acids, etc. that are necessary for plant growth and/or development).

As used herein, the terms "percent identity," "% identity" and "percent identical" refer to the relatedness of two or more nucleotide or amino acid sequences, which may be calculated by (i) comparing two optimally aligned sequences over a window of comparison, (ii) determining the number of positions at which the identical nucleic acid base (for nucleotide sequences) or amino acid residue (for proteins) occurs in both sequences to yield the number of matched positions, (iii) dividing the number of matched positions by the total number of positions in the window of comparison, and then (iv) multiplying this quotient by 100% to yield the percent identity. If the "percent identity" is being calculated in relation to a reference sequence without a particular comparison window being specified, then the percent identity is determined by dividing the number of matched positions over the region of alignment by the total length of the reference sequence. Accordingly, for purposes of the present invention, when two sequences (query and subject) are optimally aligned (with allowance for gaps in their alignment), the "percent identity" for the query sequence is equal to the number of identical positions between the two sequences divided by the total number of positions in the query sequence over its length (or a comparison window), which is then multiplied by 100%.

As used herein, the term "pest" includes any organism or virus that negatively affects a plant, including, but not limited to, organisms and viruses that spread disease, damage host plants and/or compete for soil nutrients. The term "pest" encompasses organisms and viruses that are known to associate with plants and to cause a detrimental effect on the plant's health and/or vigor. Plant pests include, but are not limited to, microbial pests, preferably bacteria and/or fungi, including oomycetes.

As used herein, the terms "pesticide" and "pesticidal" refer to agents or combinations of agents the application of which is toxic to a pest (i.e., kills a pest, inhibits the growth of a pest and/or inhibits the reproduction of a pest). Non-limiting examples of pesticides include acaricides, fungicides, herbicides, insecticides, and nematicides, etc.

As used herein, the term "plant" includes all plant populations, including, but not limited to, agricultural, horticultural and silvicultural plants. The term "plant" encompasses plants obtained by conventional plant breeding and optimization methods (e.g., marker-assisted selection) and plants obtained by genetic engineering, including cultivars protectable and not protectable by plant breeders' rights.

As used herein, the term "plant cell" refers to a cell of an intact plant, a cell taken from a plant, or a cell derived from a cell taken from a plant. Thus, the term "plant cell" includes cells within seeds, suspension cultures, embryos, meristematic regions, callus tissue, leaves, shoots, gametophytes, sporophytes, pollen and microspores.

As used herein, the term "plant part" refers to any part of a plant, including cells and tissues derived from plants. Thus, the term "plant part" may refer to any of plant components or organs (e.g., leaves, stems, roots, etc.), plant tissues, plant cells and seeds. Examples of plant parts, include, but are not limited to, anthers, embryos, flowers, fruits, fruiting bodies, leaves, ovules, pollen, rhizomes, roots, seeds, shoots, stems and tubers, as well as scions, rootstocks, protoplasts, calli and the like.

As used herein, the term "plant propagation material" refers to a plant part from which a whole plant can be generated. Examples of plant propagation materials include, but are not limited to, cuttings (e.g., leaves, stems), rhizomes, seeds, tubers and cells/tissues that can be cultured into a whole plant.

As used herein, the term "reduced disease severity" refers to a measurable reduction in the relative or absolute percentage or proportion of a sample showing symptoms of disease.

While certain aspects of the present disclosure will hereinafter be described with reference to embodiments thereof, it will be understood by those of ordinary skill in the art that various changes in form and details may be made therein without departing from the spirit and scope of the present disclosure as defined by the claims.

Compositions of the present disclosure may comprise any agriculturally acceptable carrier(s), including, but not limited to, foliar-compatible carriers, seed-compatible carriers and soil-compatible carriers. Selection of appropriate carrier materials will depend on the intended application(s) and the elements present in the composition. In some embodiments, the carrier material(s) will be selected to provide a composition in the form of a liquid, gel, slurry, or solid. In some embodiments, the carrier will consist essentially of or consist of one or more stabilizing compounds.

In some embodiments, the composition comprises one or more solid carriers. According to some embodiments, the composition comprises one or more powders (e.g., wettable powders) and/or granules. Non-limiting examples of solid carriers include clays (e.g., attapulgite clays, montmorillonite clay, etc.), peat-based powders and granules, freeze-dried powders, spray-dried powders, spray-freeze-dried powders and combinations thereof. In some embodiments, the composition comprises one or more liquid and/or gel carriers. According to some embodiments, the composition comprises one or more non-aqueous solvents. According to some embodiments, the composition comprises one or more aqueous solvents (e.g., water).

Compositions of the present disclosure comprising non-dusting granulates may be produced, e.g., as disclosed in U.S. Pat. Nos. 4,106,991 and 4,661,452 and may optionally be coated by methods known in the art. Examples of waxy coating materials are poly(ethylene oxide) products (polyethyleneglycol, PEG) with mean molar weights of 1000 to 20000; ethoxylated nonylphenols having from 16 to 50 ethylene oxide units; ethoxylated fatty alcohols in which the alcohol contains from 12 to 20 carbon atoms and in which there are 15 to 80 ethylene oxide units; fatty alcohols; fatty acids; and mono- and di- and triglycerides of fatty acids. Examples of film-forming coating materials suitable for application by fluid bed techniques are given in GB 1483591. Compositions of the present disclosure comprising liquid enzyme preparations may, for instance, be stabilized by adding a polyol such as propylene glycol, a sugar or sugar alcohol, lactic acid or boric acid according to established methods. Compositions of the present disclosure comprising enzymes may be prepared according to the method disclosed in EP 238,216.

Compositions of the present disclosure may be formulated as a granule for example as a co-granule that combines one or more enzymes. Each enzyme will then be present in more granules securing a more uniform distribution of enzymes in, for example, a detergent. This also reduces the physical segregation of different enzymes due to different particle sizes.

An embodiment of the composition of the present disclosure relates to an enzyme granule/particle comprising an enzyme. The granule is composed of a core, and optionally one or more coatings (outer layers) surrounding the core. Typically, the granule/particle size, measured as equivalent spherical diameter (volume based average particle size), of the granule is 20-2000 μm, particularly 50-1500 μm, 100-1500 μm or 250-1200 μm.

The core may include additional materials such as fillers, fibre materials (cellulose or synthetic fibres), stabilizing agents, solubilizing agents, suspension agents, viscosity regulating agents, light spheres, plasticizers, salts, lubricants and fragrances. The core may include binders, such as synthetic polymer, wax, fat, or carbohydrate. The core may comprise a salt of a multivalent cation, a reducing agent, an antioxidant, a peroxide decomposing catalyst and/or an acidic buffer component, typically as a homogenous blend. The core may consist of an inert particle with an enzyme absorbed into it, or applied onto the surface, e.g., by fluid bed coating. The core may have a diameter of 20-2000 μm, particularly 50-1500 μm, 100-1500 μm or 250-1200 μm. The core can be prepared by granulating a blend of the ingredients, e.g., by a method comprising granulation techniques such as crystallization, precipitation, pan-coating, fluid bed coating, fluid bed agglomeration, rotary atomization, extrusion, prilling, spheronization, size reduction methods, drum granulation, and/or high shear granulation.

Methods for preparing the core can be found in Handbook of Powder Technology; Particle size enlargement by C. E. Capes; Volume 1; 1980; Elsevier. Preparation methods include known feed and granule formulation technologies, e.g.:

a) Spray dried products, wherein a liquid enzyme-containing solution is atomized in a spray drying tower to form small droplets which during their way down the drying tower dry to form an enzyme-containing particulate material. Very small particles can be produced this way (Michael S. Showell (editor); *Powdered detergents*; Surfactant Science Series; 1998; vol. 71; page 140-142; Marcel Dekker).

b) Layered products, wherein the enzyme is coated as a layer around a pre-formed inert core particle, wherein an enzyme-containing solution is atomized, typically in a fluid bed apparatus wherein the pre-formed core particles are fluidized, and the enzyme-containing solution adheres to the core particles and dries up to leave a layer of dry enzyme on the surface of the core particle. Particles of a desired size can be obtained this way if a useful core particle of the desired size can be found. This type of product is described in, e.g., WO 97/23606 c) Absorbed core particles, wherein rather than coating the enzyme as a layer around the core, the enzyme is absorbed onto and/or into the surface of the core. Such a process is described in WO 97/39116.

d) Extrusion or pelletized products, wherein an enzyme-containing paste is pressed to pellets or under pressure is extruded through a small opening and cut into particles which subsequently dried. Such particles usually have a considerable size because of the material in which the extrusion opening is made (usually a plate with bore holes) sets a limit on the allowable pressure drop over the extrusion opening. Also, very high extrusion pressures when using a small opening increase heat generation in the enzyme paste, which is harmful to the enzyme (see also Michael S. Showell (editor); *Powdered detergents*; Surfactant Science Series; 1998; vol. 71; page 140-142; Marcel Dekker).

e) Prilled products, wherein an enzyme-containing powder is suspended in molten wax and the suspension is sprayed, e.g., through a rotating disk atomiser, into a cooling chamber where the droplets quickly solidify (Michael S. Showell (editor); *Powdered detergents*; Surfactant Science Series; 1998; vol. 71; page 140-142; Marcel Dekker). The product obtained is one wherein the enzyme is uniformly distributed throughout an inert material instead of being concentrated on its surface. In addition, U.S. Pat. Nos. 4,016,040 and 4,713,245 are documents relating to this technique.

f) Mixer granulation products, wherein a liquid is added to a dry powder composition of, e.g., conventional granulating components, the enzyme being introduced either via the liquid or the powder or both. The liquid and the powder are mixed and as the moisture of the liquid is absorbed in the dry powder, the components of the dry powder will start to adhere and agglomerate and particles will build up, forming granulates comprising the enzyme. Such a process is described in U.S. Pat. No. 4,106,991 and related documents EP 170360, EP 304332, EP 304331, WO 90/09440 and WO 90/09428. In a particular product of this process wherein various high-shear mixers can be used as granulators, granulates consisting of enzyme as enzyme, fillers and binders etc. are mixed with cellulose fibres to reinforce the particles to give the so-called T-granulate. Reinforced particles, being more robust, release less enzymatic dust.

g) Size reduction, wherein the cores are produced by milling or crushing of larger particles, pellets, tablets, briquettes etc. containing the enzyme. The wanted core particle fraction is obtained by sieving the milled or crushed product. Over and undersized particles can be recycled. Size reduction is described in (Martin Rhodes (editor); Principles of Powder Technology; 1990; Chapter 10; John Wiley & Sons).

h) Fluid bed granulation. Fluid bed granulation involves suspending particulates in an air stream and spraying a liquid onto the fluidized particles via nozzles. Particles hit by spray droplets get wetted and become tacky. The tacky particles collide with other particles and adhere to them and form a granule.

i) The cores may be subjected to drying, such as in a fluid bed drier. The drying preferably takes place at a product temperature of from 25 to 90° C. For some embodiments of the composition of the present disclosure comprising an enzyme it is important the cores comprising the enzyme contain a low amount of water before coating. If water sensitive enzymes are coated before excessive water is removed, it will be trapped within the core and it may affect the activity of the enzyme negatively. After drying, the cores preferably contain 0.1-10% w/w water.

The core of the enzyme granule/particle may be surrounded by at least one coating, e.g., to improve the storage stability, to reduce dust formation during handling, or for coloring the granule. The optional coating(s) may include a salt coating, or other suitable coating materials, such as polyethylene glycol (PEG), methyl hydroxy-propyl cellulose (MHPC) and polyvinyl alcohol (PVA). Examples of enzyme granules with multiple coatings are shown in WO 93/07263 and WO 97/23606.

The coating may be applied in an amount of at least 0.1% by weight of the core, e.g., at least 0.5%, 1% or 5%. The amount may be at most 100%, 70%, 50%, 40% or 30%. The coating is preferably at least 0.1 µm thick, particularly at least 0.5 µm, at least 1 µm or at least 5 µm. In a particular embodiment the thickness of the coating is below 100 µm. In a more particular embodiment the thickness of the coating is below 60 µm. In an even more particular embodiment the total thickness of the coating is below 40 µm. The coating should encapsulate the core unit by forming a substantially continuous layer. A substantially continuous layer is to be understood as a coating having few or no holes, so that the core unit it is encapsulating/enclosing has few or none uncoated areas. The layer or coating should in particular be homogeneous in thickness. The coating can further contain other materials as known in the art, e.g., fillers, antisticking agents, pigments, dyes, plasticizers and/or binders, such as titanium dioxide, kaolin, calcium carbonate or talc.

A salt coating may comprise at least 60% by weight w/w of a salt, e.g., at least 65%, at least 70%, at least 75%, at least 80%, at least 85%, at least 90%, at least 95% or at least 99% by weight w/w. The salt may be added from a salt solution where the salt is completely dissolved or from a salt suspension wherein the fine particles is less than 50 µm, such as less than 10 µm or less than 5 µm. The salt coating may comprise a single salt or a mixture of two or more salts. The salt may be water soluble, in particular having a solubility at least 0.1 grams in 100 g of water at 20° C., preferably at least 0.5 g per 100 g water, e.g., at least 1 g per 100 g water, e.g., at least 5 g per 100 g water.

The salt may be an inorganic salt, e.g., salts of sulfate, sulfite, phosphate, phosphonate, nitrate, chloride or carbonate or salts of simple organic acids (less than 10 carbon atoms, e.g., 6 or less carbon atoms) such as citrate, malonate or acetate. Examples of cations in these salts are alkali or earth alkali metal ions, the ammonium ion or metal ions of the first transition series, such as sodium, potassium, magnesium, calcium, zinc or aluminium. Examples of anions include chloride, bromide, iodide, sulfate, sulfite, bisulfite, thiosulfate, phosphate, monobasic phosphate, dibasic phosphate, hypophosphite, dihydrogen pyrophosphate, tetraborate, borate, carbonate, bicarbonate, metasilicate, citrate, malate, maleate, malonate, succinate, lactate, formate, acetate, butyrate, propionate, benzoate, tartrate, ascorbate or gluconate. In particular, alkali- or earth alkali metal salts of sulfate, sulfite, phosphate, phosphonate, nitrate, chloride or carbonate or salts of simple organic acids such as citrate, malonate or acetate may be used.

The salt in the coating may have a constant humidity at 20° C. above 60%, particularly above 70%, above 80% or above 85%, or it may be another hydrate form of such a salt (e.g., anhydrate). The salt coating may be as described in WO 00/01793 or WO 2006/034710.

Specific examples of suitable salts are NaCl ($CH_{20°\,C.}$=76%), $Na_2CO_3$ ($CH_{20°\,C.}$=92%), $NaNO_3$ ($CH_{20°\,C.}$=73%), $Na_2HPO_4$ ($CH_{20°\,C.}$=95%), $Na_3PO_4$ ($CH_{25°\,C.}$=92%), $NH_4Cl$ ($CH_{20°\,C.}$=79.5%), $(NH_4)_2HPO_4$ ($CH_{20°\,C.}$=93.0%), $NH_4H_2PO_4$ ($CH_{20°\,C.}$=93.1%), $(NH_4)_2SO_4$ ($CH_{20°\,C.}$=81.1%), KCl ($CH_{20°\,C.}$=85%), $K_2HPO_4$ ($CH_{20°\,C.}$=92%), $KH_2PO_4$ ($CH_{20°\,C.}$=96.5%), $KNO_3$ ($CH_{20°\,C.}$=93.5%), $Na_2SO_4$ ($CH_{20°\,C.}$=93%), $K_2SO_4$ ($CH_{20°\,C.}$=98%), $KHSO_4$ ($CH_{20°\,C.}$=86%), $MgSO_4$ ($CH_{20°\,C.}$=90%), $ZnSO_4$ ($CH_{20°\,C.}$=90%) and sodium citrate ($CH_{25°\,C.}$=86%). Other examples include $NaH_2PO_4$, $(NH_4)H_2PO_4$, $CuSO_4$, $Mg(NO_3)_2$ and magnesium acetate.

The salt may be in anhydrous form, or it may be a hydrated form, i.e. a crystalline salt hydrate with bound water(s) of crystallization, such as described in WO 99/32595. Specific examples include anhydrous sodium sulfate ($Na_2SO_4$), anhydrous magnesium sulfate ($MgSO_4$), magnesium sulfate heptahydrate ($MgSO_4 \cdot 7H_2O$), zinc sulfate heptahydrate ($ZnSO_4 \cdot 7H_2O$), sodium phosphate dibasic heptahydrate ($Na_2HPO_4 \cdot H_2O$), magnesium nitrate hexahydrate ($Mg(NO_3)_2(6H_2O)$), sodium citrate dihydrate and magnesium acetate tetrahydrate. Preferably the salt is applied as a solution of the salt, e.g., using a fluid bed.

Thus, in a further aspect, a composition used in the methods of the present disclosure comprises a granule, which comprises: (a) a core comprising an enzyme, and (b) optionally a coating consisting of one or more layer(s) surrounding the core.

In some embodiments, compositions of the present diclosure are applied at a rate of about 0.5 to about 100 milliliters and/or grams of composition per plant. According to some embodiments, one or more compositions of the present diclosure is/are applied in an amount sufficient to ensure each plant is treated with about/at least 0.05, 0.1, 0.125, 0.15, 0.175, 0.2, 0.225, 0.2.5, 0.275, 0.3, 0.325, 0.35, 0.375, 0.4, 0.425, 0.45, 0.475, 0.5, 0.55, 0.6, 0.65, 0.7, 0.75, 0.8, 0.85, 0.9, 0.95, 1, 1.25, 1.5, 1.75, 2, 2.25, 2.5, 2.75, 3, 3.25, 3.5, 3.75, 4, 4.25, 4.5, 4.75, 5, 5.5, 6, 6.5, 7, 7.5, 8, 8.5, 9, 9.5, 10, 20, 30, 40, 50, 60, 70, 80, 90 or 100 milliliters and/or grams of inoculant composition. According to some embodiments, one or more compositions of the present diclosure is/are applied in an amount sufficient to ensure that an average of about/at least 0.05, 0.1, 0.125, 0.15, 0.175, 0.2, 0.225, 0.2.5, 0.275, 0.3, 0.325, 0.35, 0.375, 0.4, 0.425, 0.45, 0.475, 0.5, 0.55, 0.6, 0.65, 0.7, 0.75, 0.8, 0.85, 0.9, 0.95, 1, 1.25, 1.5, 1.75, 2, 2.25, 2.5, 2.75, 3, 3.25, 3.5, 3.75, 4, 4.25, 4.5, 4.75 or 5 milliliters and/or grams of composition is applied to each plant.

In some embodiments, compositions of the present diclosure are applied at a rate of about 0.5 to about 100 milliliters and/or grams of composition per acre of treated crops. According to some embodiments, one or more compositions of the present disclosure is/are applied in an amount sufficient to ensure each acre of treated crops is treated with about/at least 0.05, 0.1, 0.125, 0.15, 0.175, 0.2, 0.225, 0.2.5, 0.275, 0.3, 0.325, 0.35, 0.375, 0.4, 0.425, 0.45, 0.475, 0.5, 0.55, 0.6, 0.65, 0.7, 0.75, 0.8, 0.85, 0.9, 0.95, 1, 1.25, 1.5, 1.75, 2, 2.25, 2.5, 2.75, 3, 3.25, 3.5, 3.75, 4, 4.25, 4.5, 4.75, 5, 5.5, 6, 6.5, 7, 7.5, 8, 8.5, 9, 9.5, 10, 20, 30, 40, 50, 60, 70, 80, 90 or 100 milliliters and/or grams of composition. According to some embodiments, one or more compositions of the present diclosure is/are applied in an amount sufficient to ensure that an average of about/at least 0.05, 0.1, 0.125, 0.15, 0.175, 0.2, 0.225, 0.2.5, 0.275, 0.3, 0.325, 0.35, 0.375, 0.4, 0.425, 0.45, 0.475, 0.5, 0.55, 0.6, 0.65, 0.7, 0.75, 0.8, 0.85, 0.9, 0.95, 1, 1.25, 1.5, 1.75, 2, 2.25, 2.5, 2.75, 3, 3.25, 3.5, 3.75, 4, 4.25, 4.5, 4.75 or 5 milliliters and/or grams of composition is applied to each acre of treated crops.

In some embodiments, compositions of the present diclosure are applied at a rate of about 0.5 to about 100 milliliters and/or grams of composition per acre of plant growth media. According to some embodiments, one or more compositions of the present diclosure is/are applied in an amount sufficient to ensure each acre of plant growth media is treated with about/at least 0.05, 0.1, 0.125, 0.15, 0.175, 0.2, 0.225, 0.2.5, 0.275, 0.3, 0.325, 0.35, 0.375, 0.4, 0.425, 0.45, 0.475, 0.5, 0.55, 0.6, 0.65, 0.7, 0.75, 0.8, 0.85, 0.9, 0.95, 1, 1.25, 1.5, 1.75, 2, 2.25, 2.5, 2.75, 3, 3.25, 3.5, 3.75, 4, 4.25, 4.5, 4.75, 5, 5.5, 6, 6.5, 7, 7.5, 8, 8.5, 9, 9.5, 10, 20, 30, 40, 50, 60, 70, 80, 90 or 100 milliliters and/or grams of composition. According to some embodiments, one or more compositions of the present diclosure is/are applied in an amount sufficient to ensure that an average of about/at least 0.05, 0.1, 0.125, 0.15, 0.175, 0.2, 0.225, 0.2.5, 0.275, 0.3, 0.325, 0.35, 0.375, 0.4, 0.425, 0.45, 0.475, 0.5, 0.55, 0.6, 0.65, 0.7, 0.75, 0.8, 0.85, 0.9, 0.95, 1, 1.25, 1.5, 1.75, 2, 2.25, 2.5, 2.75, 3, 3.25, 3.5, 3.75, 4, 4.25, 4.5, 4.75, 5, 10, 20 , 30 , 40, 50, 100, 500, 1,000, 5,000, or 10,000 milliliters and/or grams of composition is applied to each acre of plant growth media.

In some embodiments, the composition comprises a protease derived from a strain selected from the group *Alicyclobacillus, Arthrobacter, Aspergillus* (such as *Aspergillus oryzae*), *Bacillus* (such as, *Bacillus amyloliquefaciens, Bacillus clausii, Bacillus licheniformis, Bacillus mojavensis*, and *Bacillus pumilus*), *Dichomitus squalens, Fusarium oxysporum, Janibacter, Lysobacter, Meripilus giganteus, Nocardiopsis prasina, Pyrococcus furiosus, Rhizomucor miehei, Saccharomonospora viridis, Saccharothrix australiensis, Saccharothrix variisporea, Streptomyces* (such as *Streptomyces violaceoruber*), *Streptosporangium albidum, Thermoascus aurantiacus, Trichoderma reesei,* and *Zophobas afratus*.

The present invention is further described by the following numbered paragraphs:

Paragraph [1]. A method comprising foliar application of a composition comprising an effective amount of a phytoprotective agent to a plant and/or plant part.

Paragraph [2]. A method of controlling or preventing one or more plant diseases and/or plant pests in a plant or plant part and/or inducing disease resistance to a pathogen in a plant or plant part, comprising applying an effective amount of a composition comprising a phytoprotective agent to the plant or plant part.

Paragraph [3]. The method of controlling or preventing pathogenic damage and/or pest damage in a plant propagation material, a plant, part of a plant and/or plant organ, comprising applying on the plant, part of the plant, plant organ, plant propagation material or a surrounding area thereof an effective amount of a composition comprising a phytoprotective agent.

Paragraph [4]. The method of any one of paragraphs 1-3, wherein the phytoprotection agent comprises a protease.

Paragraph [5]. The method of any one of paragraphs 1-3, wherein the phytoprotective agent comprises a polypeptide having at least 70%, 75%, 80%, 81/%, 82%, 83/%, 84%, 85%, 86%, 87/%, 88%, 89%, 90%, 91/%, 92%, 93%, 94%, 95%, 96%, 97%, 97.5%, 98% 98.5%, 99%, 99.5%, or 100% sequence identity with a sequence selected from the group SEQ ID NO: 1, SEQ ID NO: 2, SEQ ID NO: 3, SEQ ID NO: 4, and SEQ ID NO: 5.

Paragraph [6]. The method of any one of paragraphs 1-3, wherein the phytoprotective agent comprises a protease derived from a strain selected from the group *Alicyclobacillus, Arthrobacter, Aspergillus oryzae, Bacillus* (such as, *Bacillus amyloliquefaciens, Bacillus clausii, Bacillus licheniformis, Bacillus mojavensis*, and *Bacillus pumilus*), *Dichomitus squalens, Fusarium oxysporum, Janibacter, Lysobacter, Meripilus giganteus, Nocardiopsis prasina, Pyrococcus furiosus, Rhizomucor miehei, Saccharomonospora viridis, Saccharothrix australiensis, Saccharothrix variisporea, Streptomyces* (such as *Streptomyces violaceoruber*), *Streptosporangium albidum, Thermoascus aurantiacus, Trichoderma reesei*, and *Zophobas atratus*.

Paragraph [7]. The method of any one of paragraphs 1-3, wherein the phytoprotective agent comprises an endopeptidase.

Paragraph [8]. The method of any one of paragraphs 1-7, wherein the plant part is foliage.

Paragraph [9]. The method of any one of paragraphs 1-8, wherein the phytoprotective agent is in an amount or concentration of about 0.0001 to about 95% or more (by weight) of the composition, for example about 0.0001, 0.0002, 0.0003, 0.0004, 0.0005, 0.0006, 0.0007, 0.0008, 0.0009, 0.001, 0.0015, 0.002, 0.0025, 0.003, 0.0035, 0.004, 0.0045, 0.005, 0.0055, 0.006, 0.0065, 0.007, 0.0075, 0.008, 0.0085, 0.009, 0.0095, 0.01, 0.015, 0.02, 0.025, 0.03, 0.035, 0.04, 0.045, 0.05, 0.06, 0.07, 0.08, 0.09, 0.1, 0.02, 0.3, 0.4, 0.5, 0.6, 0.7, 0.8, 0.9, 1 to about 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, 3, 3.1, 3.2, 3.3, 3.4, 3.5, 3.6, 3.7, 3.8, 3.9, 4, 4.1, 4.2, 4.3, 4.4., 4.5, 4.6, 4.7, 4.8, 4.9, 5, 10, 15, 20, 25, 30, 35, 40, 45, 50, 55, 60, 65, 70, 75, 80, 85, 90, 95% (by weight) of the composition.

Paragraph [10]. The method of any one of paragraphs 1-9, wherein the composition further comprises an agriculturally acceptable carrier, for example, a foliar-compatible carrier, a seed-compatible carrier, and/or a soil-compatible carrier, wherein the carrier comprises a liquid, gel, slurry, or solid, optionally:

- one or more monosaccharides, optionally arabinose, fructose and/or glucose;
- one or more disaccharides, optionally maltose, sucrose and/or trehalose;
- one or more maltodextrins, optionally one or more maltodextrins (e.g., one or more maltodextrins (each and/or collectively) having a DEV value of about 15 to about 20;
- one or more sugar alcohols, optionally arabitol, mannitol, sorbitol and/or xylitol;
- one or more humic acids, optionally potassium humate and/or sodium humate;
- one or more fulvic acids, optionally potassium fulvate and/or sodium fulvate;
- one or more hygroscopic polymers, optionally one or more albumins, alginates, celluloses, gums (e.g., cellulose gum, guar gum, gum arabic, gum combretum, xantham gum), methyl celluloses, nylons, pectins, polyacrylic acids, polycarbonates, polyethylene glycols (PEG), polyethylenimines (PEI), polylactides, polymethylacrylates (PMA), polyurethanes, polyvinyl alcohols (PVA), polyvinylpyrrolidones (PVP), propylene glycols, sodium carboxymethyl celluloses and/or starches;
- one or more oxidation control components, optionally one or more antioxidants (e.g., ascorbic acid, ascorbyl palmitate, ascorbyl stearate, calcium ascorbate, one or more carotenoids, lipoic acid, one or more phenolic compounds (e.g., one or more flavonoids, flavones and/or flavonols), potassium ascorbate, sodium ascorbate, one or more thiols (e.g., glutathione, lipoic acid and/or N-acetyl cysteine), one or more tocopherols, one or more tocotrienols, ubiquinone and/or uric acid) and/or one or more oxygen scavengers, optionally ascorbic acid and/or sodium hydrogen carbonate; and/or
- one or more UV protectants, optionally one or more lignosulfites.

Paragraph [11]. The method of any one of paragraphs 1-10, wherein the composition further comprises one or more pesticides, optionally:
- one or more acaricides, insecticides and/or nematicides, optionally one or more carbamates, diamides, macrocyclic lactones, neonicotinoids, organophosphates, phenylpyrazoles, pyrethrins, spinosyns, synthetic pyrethroids, tetronic acids and/or tetramic acids;
- one or more fungicides, optionally one or more aromatic hydrocarbons, benzimidazoles, benzthiadiazole, carboxamides, carboxylic acid amides, morpholines, phenylamides, phosphonates, quinone outside inhibitors, thiazolidines, thiophanates, thiophene carboxamides and/or triazoles;
- one or more gastropodicides, optionally one or more iron phosphates, metaldehydes, methiocarbs and/or salts;
- one or more herbicides, optionally one or more acetyl CoA carboxylase (ACCase) inhibitors, acetolactate synthase (ALS) inhibitors, acetohydroxy acid synthase (AHAS) inhibitors, photosystem II inhibitors, photosystem I inhibitors, protoporphyrinogen oxidase (PPO or Protox) inhibitors, carotenoid biosynthesis inhibitors, enolpyruvyl shikimate-3-phosphate (EPSP) synthase inhibitor, glutamine synthetase inhibitor, dihydropteroate synthetase inhibitor, mitosis inhibitors, 4-hydroxyphenyl-pyruvate-dioxygenase (4-HPPD) inhibitors, synthetic auxins, auxin herbicide salts, auxin transport inhibitors, and/or nucleic acid inhibitors;
- one or more rodenticides, optionally brodifacoum, bromadiolone, bromethalin, cholecalciferol, chlorophacinone, difethialone, diphacinone, strychnine, warfarin and/or zinc phosphide; and/or
- one or more virucides.

Paragraph [12]. The method of any one of paragraphs 1-11, wherein the composition further comprises one or more flavonoids, optionally:
- one or more anthocyanidins, optionally cyanidin, delphinidin, malvidin, pelargonidin, peonidin and/or petunidin;
- one or more anthoxanthins, optionally one or more flavones, such as apigenin, baicalein, chrysin, 7,8-dihydroxyflavone, diosmin, flavoxate, 6-hydroxyflavone, luteolin, scutellarein, tangeritin and/or wogonin; and/or flavonols, such as amurensin, astragalin, azaleatin, azalein, fisetin, furanoflavonols galangin, gossypetin, 3-hydroxyflavone, hyperoside,icariin, isoquercetin, kaempferide, kaempferitrin, kaempferol, isorhamnetin, morin, myricetin, myricitrin, natsudaidain, pachypodol, pyranoflavonols quercetin, quericitin, rhanmazin, rhamnetin, robinin, rutin, spiraeoside, troxerutin and/or zanthorhamnin;
- one or more flavanones, optionally butin, eriodictyol, hesperetin, hesperidin, homoeriodictyol, isosakuranetin, naringenin, naringin, pinocembrin, poncirin, sakuranetin, sakuranin and/or sterubin;
- one or more flavanonols, optionally dihydrokaempferol and/or taxifolin; flavans, such as flavan-3-ols (e.g., catechin (C), catechin 3-gallate (Cg), epicatechins (EC), epigallocatechin (EGC) epicatechin 3-gallate (ECg), epigallcatechin 3-gallate (EGCg), epiafzelechin, fisetinidol, gallocatechin (GC), gallcatechin 3-gallate (GCg), guibourtinidol, mesquitol, robinetinidol, theaflavin-3-gallate, theaflavin-3'-gallate, theflavin-3,3'-digallate, thearubigin), flavan-4-ols (e.g., apiforol and/or luteoforol) and/or flavan-3,4-diols (e.g., leucocyanidin, leucodelphinidin, leucofisetinidol, leucomalvidin, luecopelargonidin, leucopeonidin, leucorobinetinidin, melacacidin and/or teracacidin); and/or
- one or more isoflavonoids, optionally one or more isoflavones, such as biochanin A, daidzein, formononetin, genistein and/or glycitein; isoflavanes, such as equol, ionchocarpane and/or laxifloorane; isoflavandiols; isoflavenes, such asglabrene, haginin D and/or 2-methoxyjudaicin; coumestans, such as coumestrol, plicadin and/or wedelolactone; pterocarpans; and/or roetonoids; and/or
- one or more neoflavonoids, optionally calophyllolide, coutareagenin, dalbergichromene, dalbergin and/or nivetin; and/or
- one or more pterocarpans, optionally bitucarpin A, bitucarpin B, erybraedin A, erybraedin B, eiythrabyssin II, erthyrabissin-1, erycristagallin, glycinol, glyceollidins, glyceollins, glycyrrhizol, maackiain, medicarpin, morisianine, orientanol, phaseolin, pisatin, striatine and/or trifolirhizin.

Paragraph [13]. The method of any one of paragraphs 1-12, wherein the composition further comprises one or more water-soluble anionic surfactants and/or one or more water-insoluble anionic surfactants, optionally: one or more anionic surfactants selected from the group consisting of alkyl carboxylates (e.g., sodium stearate), alkyl sulfates (e.g., alkyl lauryl sulfate, sodium lauryl sulfate), alkyl ether sulfates, alkyl amido ether sulfates, alkyl aryl polyether sulfates, alkyl aryl sulfates, alkyl aryl sulfonates, alkyl sulfonates, alkyl amide sulfonates, alkyl aryl sulfonates, alkyl benzene sulfonates, alkyl diphenyloxide sulfonate, alpha-olefin sulfonates, alkyl naphthalene sulfonates, paraffin sulfonates, alkyl sulfosuccinates, alkyl ether sulfosuccinates, alkylamide sulfosuccinates, alkyl sulfosuccinamates, alkyl sulfoacetates, alkyl phosphates, alkyl ether phosphates, acyl sarconsinates, acyl isethionates, N-acyl taurates, N-acyl-N-alkyltaurates, benzene sulfonates, cumene sulfonates, dioctyl sodium sulfosuccinate, ethoxylated sulfosuccinates, lignin sulfonates, linear alkylbenzene sulfonates, monoglyceride sulfates, perfluorobutanesulfonate, perfluorooctanesulfonate, phosphate ester, styrene acrylic polymers, toluene sulfonates and xylene sulfonates.

Paragraph [14]. The method of any of one of paragraphs 1-13, wherein the composition further comprises one or more cationic surfactants, optionally: alkyltrimethylammonium salts (e.g., cetyl trimethylammonium bromide, cetyl trimethylammonium chloride), cetylpyridinium chloride, benzalkonium chloride, benzethonium chloride, 5-Bromo-5-nitro-1,3-dioxane, dimethyldioctadecylammonium chloride, cetrimonium bromide, dioctadecyldimethylammonium bromide and/or octenidine dihydrochloride.

Paragraph [15]. The method of any one of paragraphs 1-14, wherein the composition further comprises one or more water-soluble nonionic surfactants and/or one or more water-insoluble nonionic surfactants, optionally: alcohol ethoxylates, alkanolamides, alkanolamine condensates, carboxylic acid esters, cetostearyl alcohol, cetyl alcohol, cocamide DEA, dodecyldimethylamine oxides, ethanolamides, ethoxylates of glycerol ester and glycol esters, ethylene oxide polymers, ethylene oxide-propylene oxide copolymers, glucoside alkyl ethers, glycerol alkyl ethers, glycerol esters, glycol alkyl ethers (e.g., polyoxyethylene glycol alkyl ethers, polyoxypropylene glycol alkyl ethers), glycol alkylphenol ethers (e.g., polyoxyethylene glycol alkylphenol ethers,), glycol esters, monolaurin, pentaethylene glycol monododecyl ethers, poloxamer, polyamines, polyglycerol polyricinoleate, polysorbate, polyoxyethylenated fatty acids, polyoxyethylenated mercaptans, polyoxyethylenated polyoxyproylene glycols, polyoxyethylene glycol sorbitan alkyl esters, polyethylene glycol-polypropylene glycol copolymers, polyoxyethylene glycol octylphenol ethers, polyvinyl pynolidones, sugar-based alkyl polyglycosides, sulfoanylamides, sorbitan fatty acid alcohol ethoxylates, sorbitan fatty acid ester ethoxylates, sorbitan fatty acid ester and/or tertiary acetylenic glycols.

Paragraph [16]. The method of any one of paragraphs 1-15, wherein the composition further comprises one or more zwitterionic surfactants, optionally: 3[(3-Cholamidopropyl)dimethylammonio]-1-propanesulfonate, cocamidopropyl betaine, cocamidopropyl hydroxysultaine, phosphatidylserine, phosphatidylethanolamine, phosphatidylcholine and/or one or more sphingomyelins.

Paragraph [17]. The method of any one of paragraphs 1-16, wherein the composition further comprises one or more soaps and/or organosilicone surfactants, optionally: one or more alkali metal salts of fatty acids.

Paragraph [18]. A method of any one of paragraphs 1-9, wherein the composition comprises a granule comprising one or more enzymes, optionally wherein the granule has an average particle size of 20-2000 µm equivalent spherical diameter.

Paragraph [19]. A method of paragraph 18, wherein the composition comprises a core and optionally one or more coatings surrounding the core, wherein the core optionally comprises:
one ore more additional materials such as fillers, fibre materials (cellulose or synthetic fibres), stabilizing agents, solubilizing agents, suspension agents, viscosity regulating agents, light spheres, plasticizers, salts, lubricants and fragrances;
one or more binders, such as synthetic polymer, wax, fat, or carbohydrate;
one ore more of a salt of a multivalent cation, a reducing agent, an antioxidant, a peroxide decomposing catalyst and/or an acidic buffer component, optionally as a homogenous blend;
one ore more of an inert particle with an enzyme absorbed into it, or applied onto the surface, for example, by fluid bed coating.

Paragraph pot A method comprising foliar application of a composition comprising a phytoprotective agent to foliage of a plant, wherein said phytoprotective agent comprises a protease, wherein said composition further comprises an agriculturally acceptable carrier, wherein said composition is applied an an effective amount to control one or more diseases or pests of the plant, induce disease resistance or pest resistance of the plant, improve plant health, reduce disease severity, reduce pathogenic infection, or a combination thereof.

Paragraph [21]. The method of any one of paragraphs 1-20, wherein the disease severity is reduced by at least about 40%, 45%, 50%, 55%, 60%, 65%, 70%, 75%, 80%, 85%, 90%, 95%, 96%, 97%, 98%, 99%, or 100% compared to a plant that has not received application of the composition.

EXAMPLES

The following examples are not intended to be a detailed catalogue of all the different ways in which the present disclosure may be implemented or of all the features that may be added to the present disclosure. Subjects skilled in the art will appreciate that numerous variations and additions to the various embodiments may be made without departing from the present disclosure. Hence, the following descriptions are intended to illustrate some particular embodiments of the invention and not to exhaustively specify all permutations, combinations and variations thereof.

In the following examples, Composition 2 comprises a protease having the polypeptide sequence of SEQ ID NO: 1. Composition 4 comprises a protease having the polypeptide sequence of SEQ ID NO: 2. Composition 5 comprises a protease having the polypeptide sequence of SEQ ID NO: 3. Composition 6 comprises an amylase, used as a negative control. Composition 7 comprises a protease having the polypeptide sequence of SEQ ID NO: 4. Composition 8 comprises a protease having the polypeptide sequence of SEQ ID NO: 5.

Example 1

Inoculum Preparation: Infected tomato leaves from inoculated plants were placed in a plastic bag with a wet paper towel and incubated on a greenhouse bench at 18° C. for 24 hours. The leaves were placed in a sterile flask and rinsed with cold sterile distilled water. The spore suspension was filtered through 2 layers of cheesecloth into another sterile flask. The sporangia concentration of the inoculum was calculated using a haemocytometer and diluted with cold sterile distilled water to 10,000 sporangia per mL. The inoculum was placed into a fridge (4° C.) for 0.5-1 hour. The inoculum was removed from the fridge and allowed to warm up to room temperature for 0.5-1 hour to induce zoospore release.

Treatment Application and Inoculation of Tomato Plants: Six week old cherry tomato plants were used. There were 4 plants per treatment. Treatment plants were sprayed until run off with a 0.5% solution of Composition 2, or water, in a container and placed on a greenhouse bench for 24 hours, after which certain plants were sprayed until run off with a spore suspension of *Phytophthora infestans* (10,000 sporangia/nil) or water. They were then placed in a humidity chamber in the dark at 18° C. with 100% relative humidity for 48 hours. The plants were removed from the humidity chamber, placed on a greenhouse bench and maintained to 18° C. After 5-7 days the plants were visually rated for disease severity.

TABLE 1

Percent disease severity and disease reduction

| | Treatment | Disease Severity (%)$^X$ | Disease Reduction (%) |
|---|---|---|---|
| 1 | *P. infestans* | 67.5$^A$ | — |
| 2 | *P. infestans* + Composition 2 | 8.75$^B$ | 87 |
| 3 | Composition 2 | 0$^B$ | — |
| 4 | Water | 0$^B$ | — |

$^X$Means separation based on Tukey-Kramer HSD. Means with the same letter are not significantly different.

Example 2

Inoculum Preparation: Infected tomato leaves from inoculated plants were placed in a plastic bag with a wet paper towel and incubated on a greenhouse bench at 18° C. for 24 hours. The leaves were placed in a sterile flask and rinsed with cold sterile distilled water. The spore suspension was filtered through 2 layers of cheesecloth into another sterile flask. The sporangia concentration of the inoculum was calculated using a haemocytometer and diluted with cold sterile distilled water to 10,000 sporangia per mL. The inoculum was placed into a fridge (4° C.) for 0.5-1 hour. The inoculum was removed from the fridge and allowed to warm up to room temperature for 0.5-1 hour to induce zoospore release.

Treatment Application and Inoculation of Tomato Plants: Six week old cherry tomato plants were used. There were 4 plants per treatment. Treatment plants were sprayed until run off with a 0.5% solution of Composition 2, or water, in a container and placed on a greenhouse bench for 24 hours, after which certain plants were sprayed until run off with a spore suspension of P. infestans (10,000 sporangia/ml) or water. They were then placed in a humidity chamber in the dark at 18° C. with 100% relative humidity for 48 hours. The plants were removed from the humidity chamber, placed on a greenhouse bench and maintained to 18° C. After 5-7 days the plants were visually rated for disease severity.

TABLE 2

Percent disease severity and disease reduction

| | Treatment | Disease Severity (%)$^X$ | Disease Reduction (%) |
|---|---|---|---|
| 1 | P. infestans | $45^A$ | — |
| 2 | P. infestans + Composition 2 | $21.3^B$ | 52.8 |
| 3 | Composition 2 | $0^B$ | — |
| 4 | Water | $0^B$ | — |

$^X$Means separation based on Tukey-Kramer HSD. Means with the same letter are not significantly different.

Example 3

Inoculum Preparation: Infected tomato leaves from inoculated plants were placed in a plastic bag with a wet paper towel and incubated on a greenhouse bench at 18° C. for 24 hours. The leaves were placed in a sterile flask and rinsed with cold sterile distilled water. The spore suspension was filtered through 2 layers of cheesecloth into another sterile flask. The sporangia concentration of the inoculum was calculated using a haemocytometer and diluted with cold sterile distilled water to 10,000 sporangia per mL. The inoculum was placed into a fridge (4° C.) for 0.5-1 hour. The inoculum was removed from the fridge and allowed to warm up to room temperature for 0.5-1 hour to induce zoospore release.

Treatment Application and Inoculation of Tomato Plants: Six week old cherry tomato plants were used. There were 4 plants per treatment. Treatment plants were sprayed until run off with a 0.3% solution of Composition 2, a 0.3% solution of Composition 2 combined with a surfactant, nothing, or water, in a container and placed on a greenhouse bench for 24 hours, after which certain plants were sprayed until run off with a spore suspension of P. infestans (10,000 sporangia/ml) or water. They were then placed in a humidity chamber in the dark at 18° C. with 100% relative humidity for 48 hours. The plants were removed from the humidity chamber, placed on a greenhouse bench and maintained to 18° C. After 5-7 days the plants were visually rated for disease severity.

TABLE 3

Percent disease severity and disease reduction

| | Treatment | Disease Severity (%)$^X$ | Disease Reduction (%) |
|---|---|---|---|
| 1 | P. infestans | $90^A$ | — |
| 2 | P. infestans + Composition 2 | $13.8^B$ | 84.7 |
| 3 | P. infestans + Composition 2 + surfactant | $3.1^{CD}$ | 96.5 |
| 4 | Composition 2 | $0^D$ | — |
| 5 | Water | $0^D$ | — |

$^X$Means separation based on Tukey-Kramer HSD. Means with the same letter are not significantly different.

Example 4

Inoculum Preparation: 3 days prior to inoculation, glycerol stocks of Pseudomonas syringae were streaked onto Pseudomonas selective media and incubated at 30° C. for 48 hours. 24 hours prior to inoculation, single colonies of P. syringae were collected from the selective media and placed into 100 mL of LB media. The inoculated LB media was placed into a shaker incubator at 28° C. and 200 RPM overnight. The flasks were removed just prior to application, and 5 mL of Pst was transferred to 45 mL of 10 mM MgCl2 and shaken. Using a spectrophotometer, the absorption at $OD_{600}$ was taken. This was used to calculate the appropriate level of dilution to achieve $OD_{600}$=0.03. 200 mL of Pst solution at $OD_{600}$=0.03 were prepared, and 40 µL of Silwet was added to the inoculum.

Treatment Application and Inoculation of Tomato Plants: Seven tomato plants at four weeks old were selected per treatment. Treatment plants were sprayed until run-off with 0.5% Composition 2 or water. The plants were placed into a humidity chamber (RH 100%) for 24 hours at temperatures of 24° C. daytime and 20° C. night. 24 hours later certain plants were sprayed until runoff with a bacterial suspension of P. syringae ($OD_{600}$=0.03) or 10 mM $MgCl_2$. They were then placed in a humidity chamber (RH 100%) at 24° C. daytime and 20° C. night temperatures for 24 hours. The plants were removed from the humidity chamber, placed on a greenhouse bench and maintained at the same temperatures. After 5 days the 10 most severely infected leaves were sampled, scanned and rated for disease severity using ASSESS™ image analysis software.

TABLE 4

Percent disease severity and disease reduction

| | Treatment | Disease Severity (%)$^X$ | Disease Reduction (%) |
|---|---|---|---|
| 1 | P. syringae$^Y$ | $100.00^A$ | — |
| 2 | P. syringae + Composition 2 | $11.08^B$ | 88.93 |
| 3 | Composition 2 | $0^C$ | — |
| 4 | $MgCl_2$ | $0^C$ | — |

$^X$Means separation based on Tukey-Kramer HSD. Means with the same letter are not significantly different.
$^Y$Marked treatment had >10 leaves that could not be scanned due to leaf death and were rated 100.00% severity.

Example 5

Inoculum Preparation: 3 days prior to inoculation, glycerol stocks of P. syringae were streaked onto Pseudomonas selective media and incubated at 30° C. for 48 hours. 24 hours prior to inoculation, single colonies of P. syringae were collected from the selective media and placed into 100 mL of LB media. The inoculated LB media was placed into a shaker incubator at 28° C. and 200 RPM overnight. The flasks were removed just prior to application, and 5 mL of Pst was transferred to 45 mL of 10 mM MgCl2 and shaken. Using a spectrophotometer, the absorption at $OD_{600}$ was taken. This was used to calculate the appropriate level of dilution to achieve $OD_{600}$=0.03. 200 mL of Pst solution at $OD_{600}$=0.03 were prepared, and 40 µL of Silwet was added to the inoculum.

Treatment Application and Inoculation of Tomato Plants: Seven tomato plants at four weeks old were selected per treatment. Treatment plants were sprayed until run-off with 0.5% Composition 2 or water. The plants were placed into a humidity chamber (RH 100%) for 24 hours at temperatures of 24° C. daytime and 20° C. night. 24 hours later certain plants were sprayed until runoff with a bacterial suspension of P. syringae ($OD_{600}$=0.03) or 10 mM $MgCl_2$. They were then placed in a humidity chamber (RH 100%) at 24° C. daytime and 20° C. night temperatures for 24 hours. The plants were removed from the humidity chamber, placed on a greenhouse bench and maintained at the same temperatures. After 5 days the 10 most severely infected leaves were sampled, scanned and rated for disease severity using Assess image analysis software.

TABLE 5

Percent disease severity and disease reduction

| | Treatment | Disease Severity (%)[X] | Disease Reduction (%) |
|---|---|---|---|
| 1 | P. syringae[Y] | 100.00[A] | — |
| 2 | P. syringae + Composition 2 | 9.2[C] | 90.8 |
| 3 | Composition 2 | 0[C] | — |
| 4 | $MgCl_2$ | 0[C] | — |

[X]Means separation based on Tukey-Kramer HSD. Means with the same letter are not significantly different.
[Y]Marked treatment had >10 leaves that could not be scanned due to leaf death and were rated 100.00% severity.

Example 6

Inoculum Preparation: 3 days prior to inoculation, glycerol stocks of P. syringae were streaked onto Pseudomonas selective media and incubated at 30° C. for 48 hours. 24 hours prior to inoculation, single colonies of P. syringae were collected from the selective media and placed into 100 mL of LB media. The inoculated LB media was placed into a shaker incubator at 28° C. and 200 RPM overnight. The flasks were removed just prior to application, and 5 mL of Pst was transferred to 45 mL of 10 mM MgCl2 and shaken. Using a spectrophotometer, the absorption at $OD_{600}$ was taken. This was used to calculate the appropriate level of dilution to achieve $OD_{600}$=0.03. 200 mL of Pst solution at $OD_{600}$=0.03 were prepared, and 40 µL of Silwet was added to the inoculum.

Treatment Application and Inoculation of Tomato Plants: Seven tomato plants at four weeks old were selected per treatment. Treatment plants were sprayed until run-off with 0.3% Composition 2, 0.3% Composition 2 combined with a surfactant, or water. The plants were placed into a humidity chamber (RH 100%) for 24 hours at temperatures of 24° C. daytime and 20° C. night. 24 hours later certain plants were sprayed until runoff with a bacterial suspension of P. syringae ($OD_{600}$=0.03) or 10 mM MgCl2. They were then placed in a humidity chamber (RH 100%) at 24° C. daytime and 20° C. night temperatures for 24 hours. The plants were removed from the humidity chamber, placed on a greenhouse bench and maintained at the same temperatures. After 5 days the 10 most severely infected leaves were sampled, scanned and rated for disease severity using ASSESS™ image analysis software.

TABLE 6

Percent disease severity and disease reduction

| | Treatment | Disease Severity (%)[X] | Disease Reduction (%) |
|---|---|---|---|
| 1 | P. syringae | 15.0[A] | — |
| 2 | P. syringae + Composition 2 | 9.2[B] | 39.2 |
| 3 | P. syringae + Composition 2 + surfactant | 2.9[C] | 80.9 |
| 4 | Composition 2 | 0[C] | — |
| 5 | Water | 0[C] | — |

[X]Means separation based on Tukey-Kramer HSD. Means with the same letter are not significantly different.

Example 7

Inoculum Preparation: 7 days prior to the treatment, 2 cherry tomato plants were inoculated with P. infestans from 10-day-old Rye A+ plates. 24 hours prior to treatment, infected tomato leaves from the inoculated plants were placed in a plastic bag with a moist paper towel. The infected leaves were left on greenhouse bench at 18° C. for 24 hours. The leaves were placed in a sterile flask and rinsed with cold sterile distilled water. The spore suspension was then filtered through 2 layers of cheesecloth into another sterile flask. The sporangia concentration was calculated using haemocytometer. The inoculum concentration was adjusted to 10,000 sporangia per mL using cold sterile distilled water and inoculum was placed in fridge (4° C.) for 0.5-1 hour. After 1 hour the spore suspension was warmed to room temperature (0.5-1 hour) to induce zoospore release.

Treatment Application and Assay: Leaf disks were cut from leaves selected from 9-10 week old cherry tomato plants. Disks were dipped in 0.3% Composition solutions or water for 30 seconds. The disks were placed adaxial side up in each of the wells on plates. Each of the 24 wells contained 2 ml of 0.5% water agar. 2 plates of each treatment were prepared for a total of 48 leaf disks per treatment. 1-3 hours after treatment, the disks were wounded in the center with a sterile needle and 10 µL of P. infestans spore suspension or sterile water was dropped into the center of the disk. The plates were sealed with Parafilm and wrapped in foil. The wrapped plates were placed in an 18° C. incubator for 2 days. After 2 days, the foil was removed from the plates and they were incubated at 18° C. under light (16 hours' cool white fluorescent light and 8 hours dark). Disease severity was assessed after 5 days using the visible spectrum settings of a LEMNATEC™ SCANALYZER™.

TABLE 7

Percent healthy tissue, diseased tissue, and disease reduction, visible spectrum analysis

| | Treatment | Healthy (%)[X] | Disease (%)[X] | Disease Reduction (%) |
|---|---|---|---|---|
| 1 | P. infestans | 34.3[D] | 65.7[A] | — |
| 2 | P. infestans + Composition 2 | 62.1[C] | 37.9[B] | 42.2 |
| 3 | P. infestans + Composition 4 | 81.8[AB] | 18.2[CD] | 72.3 |
| 4 | P. infestans + Composition 5 | 71.0[C] | 28.1[BC] | 57.2 |

TABLE 7-continued

Percent healthy tissue, diseased tissue, and disease reduction, visible spectrum analysis

| | Treatment | Healthy (%)$^X$ | Disease (%)$^X$ | Disease Reduction (%) |
|---|---|---|---|---|
| 5 | P. infestans + Composition 6 | 28.2$^D$ | 71.8$^A$ | −9.3 |
| 6 | Water | 91.3$^A$ | 8.7$^D$ | — |

$^X$Means separation based on Tukey-Kramer HSD. Means with the same letter are not significantly different.

Example 8

Inoculum Preparation: 7 days prior to the treatment, 2 cherry tomato plants were inoculated with P. infestans from 10-day-old Rye A+ plates. 24 hours prior to treatment, infected tomato leaves from the inoculated plants were placed in a plastic bag with a moist paper towel. The infected leaves were left on greenhouse bench at 18° C. for 24 hours. The leaves were placed in a sterile flask and rinsed with cold sterile distilled water. The spore suspension was then filtered through 2 layers of cheesecloth into another sterile flask. The sporangia concentration was calculated using haemocytometer. The inoculum concentration was adjusted to 10,000 sporangia per mL using cold sterile distilled water and inoculum was placed in fridge (4° C.) for 0.5-1 hour. After 1 hour the spore suspension was warmed to room temperature (0.5-1 hour) to induce zoospore release.

Treatment Application and Assay: Leaf disks were cut from leaves selected from 9-10 week old cherry tomato plants. Disks were dipped in 0.3% Composition solutions or water for 30 seconds. The disks were placed adaxial side up in each of the wells on plates. Each of the 24 wells contained 2 ml of 0.5% water agar. 2 plates of each treatment were prepared for a total of 48 leaf disks per treatment. 1-3 hours after treatment, the disks were wounded in the center with a sterile needle and 10 µL of P. infestans spore suspension or sterile water was dropped into the center of the disk. The plates were sealed with Parafilm and wrapped in foil. The wrapped plates were placed in an 18° C. incubator for 2 days. After 2 days, the foil was removed from the plates and they were incubated at 18° C. under light (16 hours' cool white fluorescent light and 8 hours dark). Disease severity was assessed after 5 days using the visible spectrum settings of a LEMNATEC™ SCANALYZER™.

TABLE 8

Percent healthy tissue, diseased tissue, and disease reduction, visible spectrum analysis

| | Treatment | Healthy (%) | Disease (%) | Disease Reduction (%) |
|---|---|---|---|---|
| 1 | P. infestans | 29.5$^E$ | 70.5$^A$ | — |
| 2 | P. infestans + Composition 2 | 77.6$^B$ | 22.4$^D$ | 68.3 |
| 3 | P. infestans + Composition 4 | 82.2$^{AB}$ | 17.8$^{DE}$ | 74.7 |
| 4 | P. infestans + Composition 5 | 76.3$^{BC}$ | 23.7$^{CD}$ | 66.4 |
| 5 | P. infestans + Composition 6 | 33.4$^E$ | 66.6$^A$ | 5.5 |
| 6 | P. infestans + Composition 7 | 64.6$^{CD}$ | 35.4$^{BC}$ | 49.7 |
| 7 | P. infestans + Composition 8 | 57.1$^D$ | 42.9$^B$ | 39.1 |
| 8 | Water | 90.5$^A$ | 9.5$^E$ | — |

$^X$Means separation based on Tukey-Kramer HSD. Means with the same letter are not significantly different.

The foregoing detailed description has been given for clearness of understanding only and no unnecessary limitations should be understood therefrom as modifications will be obvious to those skilled in the art. It is not an admission that any of the information provided herein is prior art or relevant to the presently claimed inventions, or that any publication specifically or implicitly referenced is prior art.

Unless defined otherwise, all technical and scientific terms used herein have the same meaning as commonly understood by one of ordinary skill in the art to which this invention belongs.

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth and as follows in the scope of the appended claims.

That which is claimed:

1. A method comprising applying a composition comprising a phytoprotective agent to a plant and/or plant part and/or to an area surrounding said plant and/or plant part, said phytoprotective agent comprising a protease that comprises an amino acid sequence selected from SEQ ID NOs: 1-5.

2. The method of claim 1, wherein said phytoprotective agent comprises a protease that comprises the amino acid sequence set forth herein as SEQ ID NO: 1.

3. The method of claim 1, wherein said phytoprotective agent comprises a protease that comprises the amino acid sequence set forth herein as SEQ ID NO: 2.

4. The method of claim 1, wherein said phytoprotective agent comprises a protease that comprises the amino acid sequence set forth herein as SEQ ID NO: 3.

5. The method of claim 1, wherein said phytoprotective agent comprises a protease that comprises the amino acid sequence set forth herein as SEQ ID NO: 4.

6. The method of claim 1, wherein said phytoprotective agent comprises a protease that comprises the amino acid sequence set forth herein as SEQ ID NO: 5.

7. The method of claim 1, wherein said phytoprotective agent comprises a protease derived from a strain of *Alicyclobacillus, Arthrobacter, Aspergillus oryzae, Bacillus, Dichomitus squalens, Fusarium oxysporum, Janibacter, Lysobacter, Meripilus giganteus, Nocardiopsis prasina, Pyrococcus furiosus, Rhizomucor miehei, Saccharomonospora viridis, Saccharothrix australiensis, Saccharothrix variisporea, Streptomyces, Streptosporangium albidum, Thermoascus aurantiacus, Trichoderma reesei,* or *Zophobas atratus*.

8. The method of claim 1, wherein said applying comprises in-furrow application of said composition.

9. The method of claim 1, wherein said applying comprises foliar application of said composition.

10. The method of claim 1, wherein said applying comprises on-seed application of said composition.

11. The method of claim 1, wherein said composition further comprises:
one or more monosaccharides;
one or more disaccharides;
one or more maltodextrins;
one or more sugar alcohols;
one or more humic acids;
one or more fulvic acids;
one or more hygroscopic polymers;
one or more oxidation control components; and/or
one or more UV protectants.

12. The method claim 1, wherein said composition further comprises one or more additional phytoprotective agents.

13. The method of claim 1, wherein said composition further comprises one or more water-soluble anionic surfactants and/or one or more water-insoluble anionic surfactants.

14. The method of claim 1, wherein said composition further comprises one or more cationic surfactants.

15. The method of claim 1, wherein said composition further comprises one or more water-soluble nonionic surfactants and/or one or more water-insoluble nonionic surfactants.

16. The method of claim 1, wherein said composition further comprises one or more zwitterionic surfactants.

17. The method of claim 1, wherein said composition further comprises one or more soaps and/or organosilicone surfactants.

18. The method of claim 1, wherein said composition comprises granules, said granules having an average particle size of 20-2000 μm equivalent spherical diameter.

19. The method of claim 18, wherein said granules comprise a core and one or more coatings surrounding said core.

20. The method of claim 1, wherein application of said composition reduces one or more symptoms of fungal infection/infestation by at least about 40% compared to application of a control composition lacking said phytoprotective agent.

* * * * *

SEQUENCE LISTING

```
<160> NUMBER OF SEQ ID NOS: 5

<210> SEQ ID NO 1
<211> LENGTH: 286
<212> TYPE: PRT
<213> ORGANISM: Bacillus lichenformis

<400> SEQUENCE: 1

Ala Pro Ser Pro His Thr Pro Val Ser Ser Asp Pro Ser Tyr Lys Ala
1               5                   10                  15

Glu Thr Ser Val Thr Tyr Asp Pro Asn Ile Lys Ser Asp Gln Tyr Gly
            20                  25                  30

Leu Tyr Ser Lys Ala Phe Thr Gly Thr Gly Lys Val Asn Glu Thr Lys
        35                  40                  45

Glu Lys Ala Glu Lys Lys Ser Pro Ala Lys Ala Pro Tyr Ser Ile Lys
    50                  55                  60

Ser Val Ile Gly Ser Asp Asp Arg Thr Arg Val Thr Asn Thr Thr Ala
65                  70                  75                  80

Tyr Pro Tyr Arg Ala Ile Val His Ile Ser Ser Ser Ile Gly Ser Cys
```

```
                    85                  90                  95
Thr Gly Trp Met Ile Gly Pro Lys Thr Val Ala Thr Ala Gly His Cys
                100                 105                 110

Ile Tyr Asp Thr Ser Ser Gly Ser Phe Ala Gly Thr Ala Thr Val Ser
                115                 120                 125

Pro Gly Arg Asn Gly Thr Ser Tyr Pro Tyr Gly Ser Val Lys Ser Thr
            130                 135                 140

Arg Tyr Phe Ile Pro Ser Gly Trp Arg Ser Gly Asn Thr Asn Tyr Asp
145                 150                 155                 160

Tyr Gly Ala Ile Glu Leu Ser Glu Pro Ile Gly Asn Thr Val Gly Tyr
                165                 170                 175

Phe Gly Tyr Ser Tyr Thr Thr Ser Ser Leu Val Gly Thr Thr Val Thr
                180                 185                 190

Ile Ser Gly Tyr Pro Gly Asp Lys Thr Ala Gly Thr Gln Trp Gln His
                195                 200                 205

Ser Gly Pro Ile Ala Ile Ser Glu Thr Tyr Lys Leu Gln Tyr Ala Met
            210                 215                 220

Asp Thr Tyr Gly Gly Gln Ser Gly Ser Pro Val Phe Glu Gln Ser Ser
225                 230                 235                 240

Ser Arg Thr Asn Cys Ser Gly Pro Cys Ser Leu Ala Val His Thr Asn
                245                 250                 255

Gly Val Tyr Gly Gly Ser Ser Tyr Asn Arg Gly Thr Arg Ile Thr Lys
                260                 265                 270

Glu Val Phe Asp Asn Leu Thr Asn Trp Lys Asn Ser Ala Gln
                275                 280                 285

<210> SEQ ID NO 2
<211> LENGTH: 274
<212> TYPE: PRT
<213> ORGANISM: Bacillus lichenformis

<400> SEQUENCE: 2

Ala Gln Thr Val Pro Tyr Gly Ile Pro Leu Ile Lys Ala Asp Lys Val
1               5                   10                  15

Gln Ala Gln Gly Phe Lys Gly Ala Asn Val Lys Val Ala Val Leu Asp
                20                  25                  30

Thr Gly Ile Gln Ala Ser His Pro Asp Leu Asn Val Val Gly Gly Ala
            35                  40                  45

Ser Phe Val Ala Gly Glu Ala Tyr Asn Thr Asp Gly Asn Gly His Gly
    50                  55                  60

Thr His Val Ala Gly Thr Val Ala Ala Leu Asp Asn Thr Thr Gly Val
65                  70                  75                  80

Leu Gly Val Ala Pro Ser Val Ser Leu Tyr Ala Val Lys Val Leu Asn
                85                  90                  95

Ser Ser Gly Ser Gly Ser Tyr Ser Gly Ile Val Ser Gly Ile Glu Trp
                100                 105                 110

Ala Thr Thr Asn Gly Met Asp Val Ile Asn Met Ser Leu Gly Gly Ala
            115                 120                 125

Ser Gly Ser Thr Ala Met Lys Gln Ala Val Asp Asn Ala Tyr Ala Arg
        130                 135                 140

Gly Val Val Val Val Ala Ala Ala Gly Asn Ser Gly Ser Ser Gly Asn
145                 150                 155                 160

Thr Asn Thr Ile Gly Tyr Pro Ala Lys Tyr Asp Ser Val Ile Ala Val
                165                 170                 175
```

```
Gly Ala Val Asp Ser Asn Ser Asn Arg Ala Ser Phe Ser Ser Val Gly
            180                 185                 190

Ala Glu Leu Glu Val Met Ala Pro Gly Ala Gly Val Tyr Ser Thr Tyr
        195                 200                 205

Pro Thr Asn Thr Tyr Ala Thr Leu Asn Gly Thr Ser Met Ala Ser Pro
    210                 215                 220

His Val Ala Gly Ala Ala Leu Ile Leu Ser Lys His Pro Asn Leu
225                 230                 235                 240

Ser Ala Ser Gln Val Arg Asn Arg Leu Ser Ser Thr Ala Thr Tyr Leu
            245                 250                 255

Gly Ser Ser Phe Tyr Tyr Gly Lys Gly Leu Ile Asn Val Glu Ala Ala
            260                 265                 270

Ala Gln

<210> SEQ ID NO 3
<211> LENGTH: 269
<212> TYPE: PRT
<213> ORGANISM: Bacillus clausii

<400> SEQUENCE: 3

Ala Gln Ser Val Pro Trp Gly Ile Ser Arg Val Gln Ala Pro Ala Ala
1               5                   10                  15

His Asn Arg Gly Leu Thr Gly Ser Gly Val Lys Val Ala Val Leu Asp
            20                  25                  30

Thr Gly Ile Ser Thr His Pro Asp Leu Asn Ile Arg Gly Gly Ala Ser
        35                  40                  45

Phe Val Pro Gly Glu Pro Ser Thr Gln Asp Gly Asn Gly His Gly Thr
    50                  55                  60

His Val Ala Gly Thr Ile Ala Ala Leu Asn Asn Ser Ile Gly Val Leu
65                  70                  75                  80

Gly Val Ala Pro Ser Ala Glu Leu Tyr Ala Val Lys Val Leu Gly Ala
                85                  90                  95

Ser Gly Ser Gly Ser Val Ser Ser Ile Ala Gln Gly Leu Glu Trp Ala
            100                 105                 110

Gly Asn Asn Gly Met His Val Ala Asn Leu Ser Leu Gly Ser Pro Ser
        115                 120                 125

Pro Ser Ala Thr Leu Glu Gln Ala Val Asn Ser Ala Thr Ser Arg Gly
    130                 135                 140

Val Leu Val Val Ala Ala Ser Gly Asn Ser Gly Ala Gly Ser Ile Ser
145                 150                 155                 160

Tyr Pro Ala Arg Tyr Ala Asn Ala Met Ala Val Gly Ala Thr Asp Gln
                165                 170                 175

Asn Asn Asn Arg Ala Ser Phe Ser Gln Tyr Gly Ala Gly Leu Asp Ile
            180                 185                 190

Val Ala Pro Gly Val Asn Val Gln Ser Thr Tyr Pro Gly Ser Thr Tyr
        195                 200                 205

Ala Ser Leu Asn Gly Thr Ser Met Ala Thr Pro His Val Ala Gly Ala
    210                 215                 220

Ala Ala Leu Val Lys Gln Lys Asn Pro Ser Trp Ser Asn Val Gln Ile
225                 230                 235                 240

Arg Asn His Leu Lys Asn Thr Ala Thr Ser Leu Gly Ser Thr Asn Leu
                245                 250                 255

Tyr Gly Ser Gly Leu Val Asn Ala Glu Ala Ala Thr Arg
            260                 265
```

<210> SEQ ID NO 4
<211> LENGTH: 268
<212> TYPE: PRT
<213> ORGANISM: Bacillus halodurans

<400> SEQUENCE: 4

```
Gln Thr Val Pro Trp Gly Ile Ser Phe Ile Asn Thr Gln Gln Ala His
1               5                   10                  15

Asn Arg Gly Ile Phe Gly Asn Gly Ala Arg Val Ala Val Leu Asp Thr
            20                  25                  30

Gly Ile Ala Ser His Pro Asp Leu Arg Ile Ala Gly Gly Ala Ser Phe
        35                  40                  45

Ile Ser Ser Glu Pro Ser Tyr His Asp Asn Gly His Gly Thr His
50                  55                  60

Val Ala Gly Thr Ile Ala Ala Leu Asn Asn Ser Ile Gly Val Leu Gly
65                  70                  75                  80

Val Ala Pro Ser Ala Asp Leu Tyr Ala Val Lys Val Leu Asp Arg Asn
                85                  90                  95

Gly Ser Gly Ser Leu Ala Ser Val Ala Gln Gly Ile Glu Trp Ala Ile
            100                 105                 110

Asn Asn Asn Met His Ile Ile Asn Met Ser Leu Gly Ser Thr Ser Gly
        115                 120                 125

Ser Ser Thr Leu Glu Leu Ala Val Asn Arg Ala Asn Asn Ala Gly Ile
130                 135                 140

Leu Leu Val Gly Ala Ala Gly Asn Thr Gly Arg Gln Gly Val Asn Tyr
145                 150                 155                 160

Pro Ala Arg Tyr Ser Gly Val Met Ala Val Ala Ala Val Asp Gln Asn
                165                 170                 175

Gly Gln Arg Ala Ser Phe Ser Thr Tyr Gly Pro Glu Ile Glu Ile Ser
            180                 185                 190

Ala Pro Gly Val Asn Val Asn Ser Thr Tyr Thr Gly Asn Arg Tyr Val
        195                 200                 205

Ser Leu Ser Gly Thr Ser Met Ala Thr Pro His Val Ala Gly Val Ala
210                 215                 220

Ala Leu Val Lys Ser Arg Tyr Pro Ser Tyr Thr Asn Asn Gln Ile Arg
225                 230                 235                 240

Gln Arg Ile Asn Gln Thr Ala Thr Tyr Leu Gly Ser Pro Ser Leu Tyr
                245                 250                 255

Gly Asn Gly Leu Val His Ala Gly Arg Ala Thr Gln
            260                 265
```

<210> SEQ ID NO 5
<211> LENGTH: 273
<212> TYPE: PRT
<213> ORGANISM: Bacillus clausii

<400> SEQUENCE: 5

```
Ala Gln Ser Val Pro Trp Gly Ile Ser Arg Val Gln Ala Pro Ala Ala
1               5                   10                  15

His Asn Arg Gly Leu Thr Gly Ser Gly Val Lys Val Ala Val Leu Asp
            20                  25                  30

Thr Gly Ile Ser Thr His Pro Asp Leu Asn Ile Arg Gly Gly Ala Ser
        35                  40                  45

Phe Val Pro Gly Glu Pro Ser Thr Gln Asp Gly Asn Gly His Gly Thr
50                  55                  60
```

```
His Ala Ala Gly Thr Ile Ala Ala Leu Asn Asn Ser Ile Gly Val Leu
65              70              75                  80

Gly Val Ala Pro Ser Ala Glu Leu Tyr Ala Val Lys Val Leu Gly Ala
                85              90              95

Ser Gly Ser Gly Ser Val Ser Ala Ile Ala Gln Gly Leu Glu Trp Ala
            100             105             110

Gly Asn Asn Gly Met His Val Ala Asn Leu Ser Leu Gly Ser Pro Ser
        115             120             125

Pro Ser Ala Thr Leu Glu Gln Ala Val Asn Ser Ala Thr Ser Arg Gly
    130             135             140

Val Leu Val Val Ala Ala Ser Gly Asn Ser Gly Ala Gly Ser Ile Ser
145             150             155             160

Tyr Pro Ala Arg Tyr Ala Asn Ala Met Ala Val Gly Ala Thr Asp Gln
            165             170             175

Asn Asn Asn Arg Ala Ser Phe Ser Gln Tyr Gly Ala Gly Leu Asp Ile
            180             185             190

Val Ala Pro Gly Val Asn Val Gln Ser Thr Tyr Pro Gly Ser Thr Tyr
        195             200             205

Ala Ser Leu Asn Gly Thr Ser Met Ala Thr Pro His Val Ala Gly Ala
    210             215             220

Ala Ala Leu Val Lys Gln Lys Asn Pro Ser Trp Ser Asn Val Gln Ile
225             230             235             240

Arg Asn His Leu Lys Asn Thr Ala Thr Ser Leu Gly Ser Thr Asn Leu
            245             250             255

Tyr Gly Ser Gly Leu Val Asn Ala Glu Ala Ala Thr Arg His His His
            260             265             270

His
```

UNITED STATES PATENT AND TRADEMARK OFFICE
CERTIFICATE OF CORRECTION

| | |
|---|---|
| PATENT NO. | : 11,812,747 B2 |
| APPLICATION NO. | : 16/965054 |
| DATED | : November 14, 2023 |
| INVENTOR(S) | : Inch et al. |

It is certified that error appears in the above-identified patent and that said Letters Patent is hereby corrected as shown below:

In the Claims

Claim 6 (Column 29, Lines 55-57) should read as follows:
6. The method of claim 1, wherein said phytoprotective agent comprises a protease that comprises the amino acid sequence set forth herein as SEQ ID NO: 5.

Signed and Sealed this
Ninth Day of January, 2024

*Katherine Kelly Vidal*

Katherine Kelly Vidal
*Director of the United States Patent and Trademark Office*